United States Patent
Wu et al.

(10) Patent No.: US 8,008,031 B2
(45) Date of Patent: Aug. 30, 2011

(54) COMPETITIVE RECEPTOR BINDING ASSAY FOR DETECTING BETA-GLUCANS

(75) Inventors: Mei-Li Wu, Neipu (TW); Hso-Chi Chaung, Neipu (TW); Tzou-Chi Huang, Neipu (TW); Wen-Bin Chung, Neipu (TW); Hui-Ju Hung, Neipu (TW)

(73) Assignee: National Pingtung University of Science and Technology (TW)

( * ) Notice: Subject to any disclaimer, the term of this patent is extended or adjusted under 35 U.S.C. 154(b) by 828 days.

(21) Appl. No.: 11/959,550

(22) Filed: Dec. 19, 2007

(65) Prior Publication Data

US 2009/0162872 A1    Jun. 25, 2009

(51) Int. Cl.
*G01N 33/567* (2006.01)
*G01N 33/566* (2006.01)
*G01N 33/549* (2006.01)
*G01N 33/00* (2006.01)

(52) U.S. Cl. ........ 435/7.21; 435/7.9; 435/7.92; 435/7.93

(58) Field of Classification Search ........................ None
See application file for complete search history.

(56) References Cited

U.S. PATENT DOCUMENTS

| | | | | |
|---|---|---|---|---|
| 4,665,020 | A | * | 5/1987 | Saunders .................. 435/7.4 |
| 5,698,448 | A | * | 12/1997 | Soldin ...................... 436/503 |
| 6,444,448 | B1 | * | 9/2002 | Wheatcroft et al. ......... 435/101 |
| 7,425,548 | B2 | * | 9/2008 | Nair et al. .................. 514/60 |

OTHER PUBLICATIONS

Viriyakosol et al., Innate Immunity to the Pathogenic Fungus *Coccidioides posadasii* is Dependent on Toll-Like Receptor 2 and Dectin-1. Infection and Immunity, 73, 1553-1560, 2005.*
Brown and Gordon, 2003, Immunity 19(3):311-315.
Herre et al., 2004, Molecular Immunology 40(12):869-876.
Megazyme from Megazyme International Ireland Ltd., Bray Business Park, Bray, Co. Wicklow, Ireland, 2006.
Office Action with search report dated Jan. 5, 2011, corresponding ROC (Taiwan) Patent Application No. 096148729.
Adachi, et al., Characterization of β-Glucan Recognition Site on C-Type Lectin, Dectin 1, Infection and Immunity, vol. 72(7), Jul. 2004, p. 4159-4171.
Brown, et al., Abstract of Immune recognition: a new receptor for β-glucans, Nature 413, pp. 36-37 (Sep. 6, 2001).
Brown, et al., Dectin-1 Mediates the Biological Effects of β-Glucans, J. of Exp. Med., vol. 197(9), pp. 1119-1124 (May 5, 2003).
Graham, et al. Abstract of Soluble Detin-1 as a tool to detect β-glucans, J. of Immun. Methods, vol. 314(1-2), pp. 164-169, Jul. 31, 2006.

* cited by examiner

*Primary Examiner* — Elly-Gerald Stoica
(74) *Attorney, Agent, or Firm* — Robert C. Haldiman; Husch Blackwell LLP

(57) ABSTRACT

The present invention provides a method for detecting a beta-glucan having immunomodulatory activity in a human cell, which uses a test cell line that stably expresses human dectin-1 molecule on the cell surface and does not express other glucan receptors and a specific amount of a marker beta-glucan that specifically binds to human dectin-1 molecule for detection.

11 Claims, 5 Drawing Sheets

COMPETITIVE RECEPTOR BINDING ASSAY FOR DETECTING BETA-GLUCANS

BACKGROUND OF THE INVENTION

1. Field of the Invention

The invention relates to a method for detecting a beta-glucan having affinity to dectin-1 receptor in a human cell; more particularly, a method for quantifying the amounts of beta-glucan having affinity to dectin-1 receptor in a human cell.

2. Description of the Related Art

Beta-glucan, a major component of the cell wall of fungi or yeasts, has been proven to have the ability to stimulate a macrophage secrete cytokines and strengthen the function of phagocytosis. The immunoregulation of glucan depends on the degree of branch, the length of polymer and the structure thereof.

Beta-glucans can be classified as particulate forms and soluble forms according to different solubility. A particulate beta-glucan, such as zymosan, usually has a larger molecular size and a soluble glucan, such as glucan phosphate, usually has a smaller molecular size. Either form of beta-glucan has the immunomodulatory functions once beta-glucan binds to the carbohydrate-binding domain of dectin-1 that is known as the exclusive receptor of beta-glucan. The binding of beta-glucan to dectin-1 initiates the signal transduction in an activating cell and thus enhances its productions of reactive oxygen species (ROS) and phagocytosis (Brown and Gordon, 2003, Immunity 19(3):311-315).

The beta-glucans with main chain of beta 1,3 linkage is known as beta 1,3-glucan, which may comprises beta 1,6 branch linkages (beta 1,3/1,6-glucan) has the best immunomodulatory functions. On the other hand, neither a glucan comprising a beta 1,4 branch linkage nor a glucan comprising less than 7 residues is shown to bind to dectin-1 and acts as an immunomodulator (Herre et al., 2004, Molecular Immunology 40(12):869-876). Thus, the immunomodulatory functions of beta-glucans depend on their structures or, in precisely speaking, their binding affinity to the receptor, denctin-1.

In another aspect, an antigen presenting cell, such as a macrophage or a dendritic cell, highly expresses denctin-1. Dectin-1 has been found to be the exclusive receptor of beta-glucan. It is able to recognize a beta-glucan with a specific configuration. However, it has been shown that the gene polymorphism of dectin-1 between different species affects its ability to recognize beta-glucan and thus impacts the immunomodulatory activities of different beta-glucan when applied in different mammals. The similarity in amino acid sequences of mouse dectin-1 and human dectin-1 is only about 60%, so an animal model established on mice fails to screen and identify the beta-glucans having immunomodulatory activities in humans.

The conventional methods or the current quantitative commercial assay (Megazyme from Megazyme International Ireland Ltd., Bray Business Park, Bray, Co. Wicklow, Ireland) for detecting beta-glucans is on the basis of the chemical structure, with those beta-glucans can be digested by exo-beta 1,3 gluconase and beta-glucosidase (Megazyine Assay Procedure). However, the beta-glucan having immunomodulatory activity cannot be identified. A rapid and effective method is needed for detecting a beta-glucan having immunomodulatory activity in a human cell.

SUMMARY OF THE INVENTION

The invention provides a method for rapidly detecting a beta-glucan having immunomodulatory activity in a human cell.

One object of the invention is to provide a method for detecting a beta-glucan having immunomodulatory activity in a human cell, which comprises the steps of:

(a) providing
- a test cell line that stably expresses human dectin-1 molecule on the cell surface and does not express other glucan receptors,
- a test target, and
- a marker beta-glucan that specifically binds to human dectin-1 molecule;

(b) contacting the test target and a specific amount of the marker beta-glucan with the test cell line in a test mixture so that the marker beta-glucan or the beta-glucan having immunomodulatory activity in a human cell in the test target, if any, forms a complex with the test cell line;

(c) contacting the specific amount of the marker beta-glucan with the test cell line in a reference mixture so that the marker beta-glucan forms a complex with the test cell line;

(d) removing the test target and the marker beta-glucan which do not form a complex with the test cell line in the test mixture in (b) and the reference mixture in (c);

(e) detecting the amounts of the marker beta-glucan in the test mixture and the reference mixture; and (f) comparing the amount of the marker beta-glucan in the test mixture and that in the reference mixture, wherein the test target is identified to contain the beta-glucan having immunomodulatory activity in a human cell when the amount of the marker beta-glucan in the test mixture is less than that in the reference mixture.

Preferably, the method according to the invention is for quantifying a beta-glucan having immunomodulatory activity in a human cell.

DETAILED DESCRIPTION OF THE INVENTION

Figure 1:
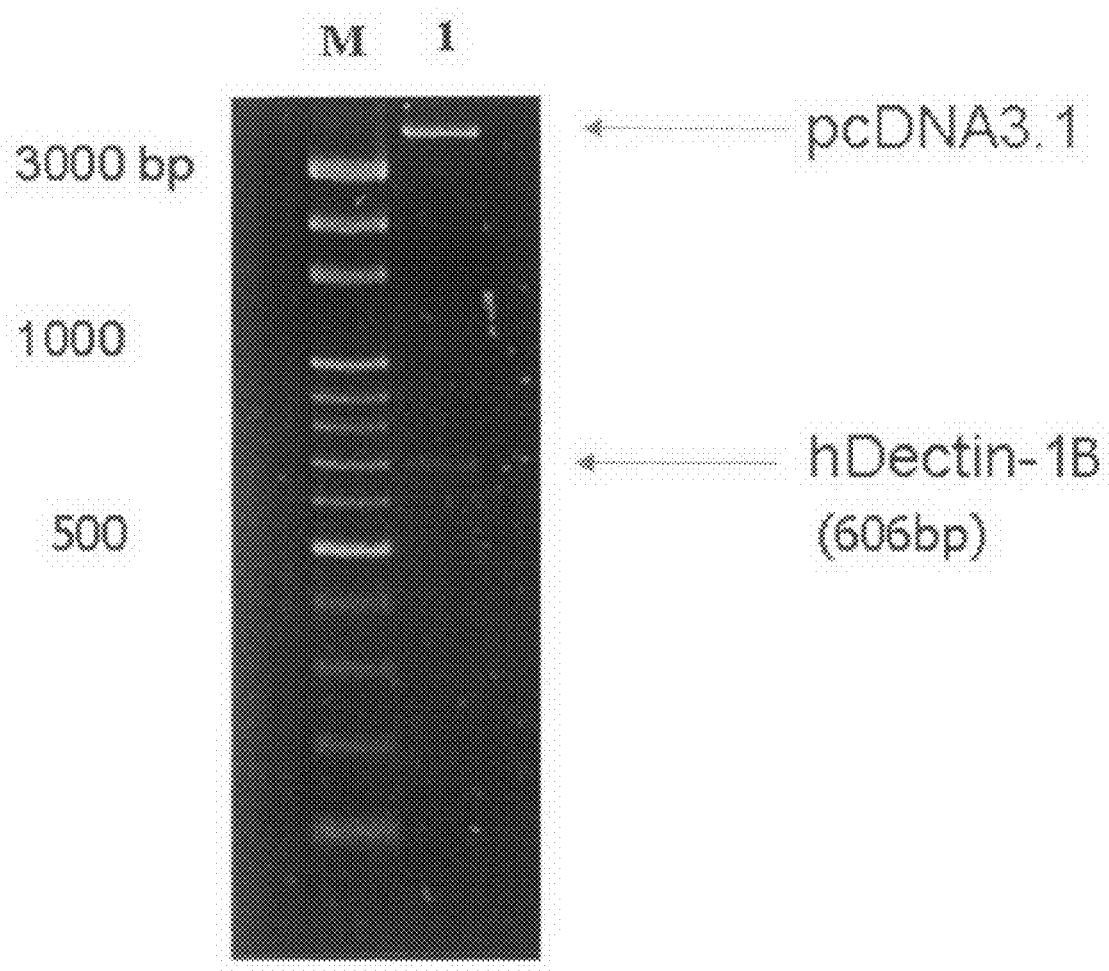
FIG. 1 shows the gel electrophoresis of DNA fragments of pcDNA3.1 with human Dectin-1 cDNA (606 bp) after digestion with BamH I and Xba I. The cDNA of human Dectin-1 was amplified and cloned into the expression vector pcDNA3.1/NV5-His TOPO TA. The pcDNA3.1 vector with human Dectin-1 cDNA was digested with BamH I and Xba I then electrophoretic analysis in 1% agarose gel (lane 1). Lane M showed DNA marker with 100 bp intervals.

The invention relates to a method for rapidly detecting a beta-glucan having immunomodulatory activity in a human cell, which comprises the steps of
(a) providing
a test cell line that stably expresses human dectin-1 molecule on the cell surface and does not express other glucan receptors,
a test target, and
a marker beta-glucan that specifically binds to human dectin-1 molecule;
(b) contacting the test target and a specific amount of the marker beta-glucan with the test cell line in a test mixture so that the marker beta-glucan or the beta-glucan having immunomodulatory activity in a human cell in the test target, if any, forms a complex with the test cell line;
(c) contacting the specific amount of the marker beta-glucan with the test cell line in a reference mixture so that the marker beta-glucan forms a complex with the test cell line;
(d) removing the test target and the marker beta-glucan which do not form a complex with the test cell line in the test mixture in (b) and the reference mixture in (c);
(e) detecting the amounts of the marker beta-glucan in the test mixture and the reference mixture; and
(f) comparing the amount of the marker beta-glucan in the test mixture and that in the reference mixture, wherein the test target is identified to contain the beta-glucan having immunomodulatory activity in a human cell when the amount of the marker beta-glucan in the test mixture is less than that in the reference mixture.

As used herein, the term "beta-glucan" refers to a polysaccharide of D-glucose monomers linked by beta 1,3-glycosidic bonds. Glucans are polysaccharides that only contain glucose as structural components. Beta 1,3-glucans are polysaccharides comprising glucose rings connected at positions 1 and 3 and known as "backbone". The most active form of beta 1,3-glucans contains 1,6 side-chains in addition to its beta 1,3-glucan backbone and is known as a beta-1,3/1,6 glucan. It is suggested that the configuration of the beta-glucan, including the frequency, location, and length of the side-chains, rather than the backbone of beta-glucans only, determines their immunomodulatory activities. The beta-glucan to be detected according to the invention can be a known substance or a substance which has not been identified yet.

Preferably, the beta-glucan is selected from the group consisting of soluble beta-glucan and particulate beta-glucan. Either form of beta-glucan can have differentially immunomodulatory activities, depending on the types of activating cells and with/without the coordinating receptors, such as toll-like receptor 2.

Preferably, the human cell according to the invention is an antigen presenting cell. More preferably, the human cell is selected from the group consisting of macrophage, dendritic cell, natural killer cell, M cell, B cell and T cell.

Dectin-1 molecule is a specific receptor for recognizing beta-glucan, and is expressed on the surface of phagocytic cells. Only when binding to dectin-1, the beta-glucan shows forward immunomodulatory functions.

As used herein, the term "test cell line" refers to a cell line that is used for assaying the beta-glucan having immunomodulatory activity in the human cell. The test cell line according to the invention plays the role of human immune cells for assaying the binding between the human immune cells and the beta-glucan. The test cell line according to the invention stably expresses human dectin-1 molecule on the cell surface as a receptor and does not express other glucan receptors. Preferably, the test cell line is a cell line transformed with the human dectin-1 gene. More preferably, the test cell line is derived from a non-immune cell. In one preferred embodiment of the invention, the test cell line is derived from the kidney.

In one preferred embodiment of the invention, the test cell line is attached to the surface of a carrier. As used herein, the term "carrier" refers to an inert support that does not react with the beta-glucan or interfere with the binding between the test cell line and the beta-glucan. For example, the carrier can be a resin or glass. The means to attach the test cell line to the surface of a carrier is well known to persons of ordinary skill in the art. For example, the coating method used in an enzyme-linked immunosorbent assay system can be utilized.

As used herein, the term "test target" refers to a sample in which the presence of beta-glucan having immunomodulatory activity in a human cell is to be detected. The target may be a material, mixture or extract derived from animals, plants or microorganisms, preferably a mixture or extract, and more preferably a mixture or extract derived from fungi. In one preferred embodiment of the invention, the test target is derived from food.

As used herein, the term "marker beta-glucan" refers to an identified beta-glucan that specifically binds to human dectin-1 molecule. Preferably, the marker beta-glucan has a beta 1,3 linkage; more preferably, the marker beta-glucan has a beta 1,3 and a beta 1,6 linkages. Most preferably, the maker beta-glucan is selected from the group consisting of zymosan, laminarin, glucan phosphate, pustulan, lichenan, scleroglucan and barley glucan. For easy detection, the marker beta-glucan preferably comprises a marker. As used herein, the term "marker" refers to a substance that emits a signal where the presence and/or the amount of the marker beta-glucan can be detected. The marker preferably comprises a molecule selected from the group consisting of dye, fluorescence, luminescence, enzyme, or reporter protein. Preferably, the marker comprises a fluorescence moiety. In one preferred embodiment of the invention, the marker comprises a molecule selected from the group consisting of fluorescein isothiocyanate, allophycocyanin, phycoerythrin, cyanine-3, cyanine-5, biotin, horseradish peroxidase, and beta-glucosidase.

According to the invention, the marker beta-glucan is provided in a specific amount. Preferably, the specific amount of the marker beta-glucan is that saturated to the test cell line. On the basis of the amount of human dectin-1 expressed on the surface of the test cell line, artisans skilled in the field can adjust the specific amount of the marker beta-glucan. In one preferred embodiment of the invention, the specific amount of the marker beta-glucan is more than about 10 times the number of the test cell line.

The test target and the marker beta-glucan or the marker beta-glucan only is contacted with the test cell line in a test mixture or in a reference mixture in step (b) or (c) according to the invention. The contacting in steps (b) and (c) can be in a manner conventionally known in the art. For example, the contacting is under an appropriate condition, such as suitable ion strength, pH value and temperature, so that the test target or the marked beta-glucan and the test cell line form a complex if the beta-glucan having immunomodulatory activity in a human cell is present in the test target.

The test target and the marker beta-glucan which do not form a complex with the test cell line in the test mixture and the reference mixture in step (b) and (c) are removed in step (d). The removal can be performed by using a method conventionally known to persons of ordinary skill in the art. For example, the unreacted molecules can be removed by washing.

The amounts of the marker beta-glucan in the test mixture and the reference mixture are detected in step (e). The marker beta-glucan can be detected by conventional methods according to the species of the signal of the reporter. For instance, visible light/UV spectrophotometer, fluorescence spectrophotometer, luminescence spectrophotometer and flow cytometry can be used to detect the reporter. Preferably, the amount of the marker beta-glucan in step (d) is detected by a flow cytometry.

In one embodiment of the invention, an enzyme-linked immunosorbent assay (ELISA) system is used to detect the beta-glucan having immunomodulatory activity in a human cell. The ELISA system can detect multiple samples in one manipulation. In addition, the system is convenient, and its reagents and procedures have been established. Preferably, a cell-based enzyme-linked immunosorbent assay system is used.

Preferably, the method according to the invention is for quantifying a beta-glucan having immunomodulatory activity in a human cell.

For the purpose of quantification, step (a) further comprises providing various of a standard beta-glucan that specifically binds to human dectin-1 molecule. As used herein, the term "standard beta-glucan" refers to a beta-glucan that is proven to specifically bind to human dectin-1 molecule, and the amount is determined. Preferably, the standard beta-glucan has a beta 1,3 linkage; more preferably, the marker beta-glucan has a beta 1,3 and a beta 1,6 linkages. Most preferably, the standard beta-glucan is selected from the group consisting of zymosan, laminarin, glucan phosphate, pustulan, lichenan, scleroglucan and barley glucan. The standard beta-glucan and the marker beta-glucan according to the invention can be the same or different. Various known amounts of the standard beta-glucan according to the invention are provided in a range that encompasses the predicted amount of the beta-glucan having immunomodulatory activity in a human cell in the test target.

For the purpose of quantification, step (b) or (c) further comprises contacting various known amounts of the standard beta-glucan and specific amount of the marker beta-glucan with the test cell line in various standard mixtures so that the marker beta-glucan and the standard beta-glucan forms a complex with the test cell line. The conditions of the contact of the standard beta-glucan and the maker beta-glucan with the test cell line are preferably the same as those in a test mixture and in a reference mixture according to the invention.

For the purpose of quantification, step (d) further comprises removing the standard beta-glucan and the marker beta-glucan which do not form a complex with the test cell line in the standard mixtures. The conditions of removal are preferably the same as those in a test mixture and in a reference mixture according to the invention.

For the purpose of quantificaiton, step (e) further comprises detecting the amount of the marker beta-glucan in the standard mixtures, and obtaining a regression curve of the amount of the standard beta-glucan versus the amount of the marker beta-glucan. The conditions of detections are preferably the same as those in a test mixture and in a reference mixture according to the invention. The regression curve is preferably established with the assistance of computer, and an equation is preferably established.

For the purpose of quantificaiton, step (f) further comprises quantifying the amount of the beta-glucan having immunomodulatory activity in a human cell by comparing the amount of the marker beta-glucan in the test mixture and the regression curve in step (e). The amount of the beta-glucan having immunomodulatory activity is quantified by conversing the parameter of the equation of the regression curve with the amount of the marker beta-glucan in the test mixture.

The method according to invention is for detecting the beta-glucan specifically binding to human dectin-1 molecule. The method according to the invention uses a cell line. Protein purification is avoided. Furthermore, the regression coefficient established in one example of the invention reaches 0.9999. Therefore, the sensitivity of the method according to the invention is quite satisfactory.

The following examples are given for the purpose of illustration only and are not intended to limit the scope of the present invention.

EXAMPLE

Test Cell Line

A recombinant human dectin-1 gene (606 bp) was constructed according to hDectin-1 (Genbank accection No. AF400596, Willment et al., 2001). A pair of primers were designed with Expert Sequence Analysis software and applied in a polymerase chain reaction with a template of kidney cDNA (Clontech®). The amplified product was purified and ligated with an expression vector from pcDNA3.1/NV5-his TOPO TA Expression Kit® (Invitrogen®, Valencia, Calif., USA). The constructed expression vector was transformed into *Escherichia coli* cells and the colonies having the inserted dectin-1 gene were selected. The plasmid was further purified and subjected to BamH I and Xba I restriction enzyme digestion. The DNA was assayed with gel electrophoresis and shown in FIG. 1. The sequence was further confirmed by sequencing.

HEK293 cell line (derived from human embryonic kindney) was cultured in a DMEM medium at 37° C./5% $CO_2$. The cells were moved to a serum-free and antibiotic-free medium, and transfected with the plasmid comprising hDectin-1 gene constructed as mentioned above. After 24 hours, a G418 analog was added to the medium to screen the expression.

Marker Beta-Glucan

A commercialized FITC-zymosan was taken as a marker beta-glucan.

To assay the binding between the marker beta-glucan and the test cell line, sterilized cover glass was positioned in the medium, and 1 mL of 1% gelatin was added to react at 37° C. for 30 min. After removing gelatin, medium containing 600 μg/mL G418 was added to culture the cells at 37° C./5% $CO_2$. FITC-zymosan (10 particles/cell) was then added to the medium at 37° C. for 30 min. The unreacted FITC-zymosan was removed by washing the cells with PBS three times.

Figure 2A:
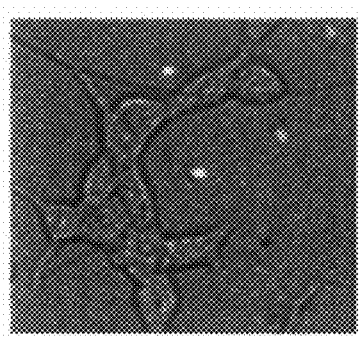
FIG. 2A shows the confocal microscopic view of HEK293 as the control cells without transfection of human Dectin-1.
Figure 2B:
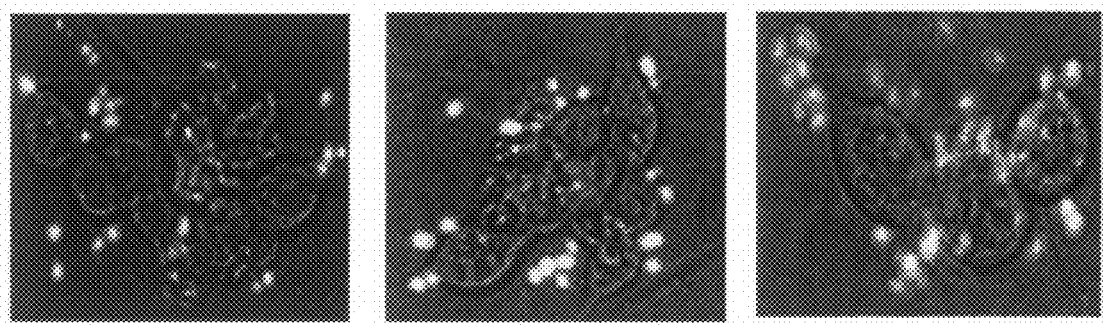
FIG. 2B shows the fluorescent microscopic view of HEK293 expressing human Dectin-1 fused with 6-histidine on the cell surface, which can recognize FITC-zymosan.

The cells were observed with a confocal microscope and shown in FIG. 2. It is shown that FITC-zymosan has the ability to bind to HEK293 expressing human dectin-1 gene.

Figure 3A:
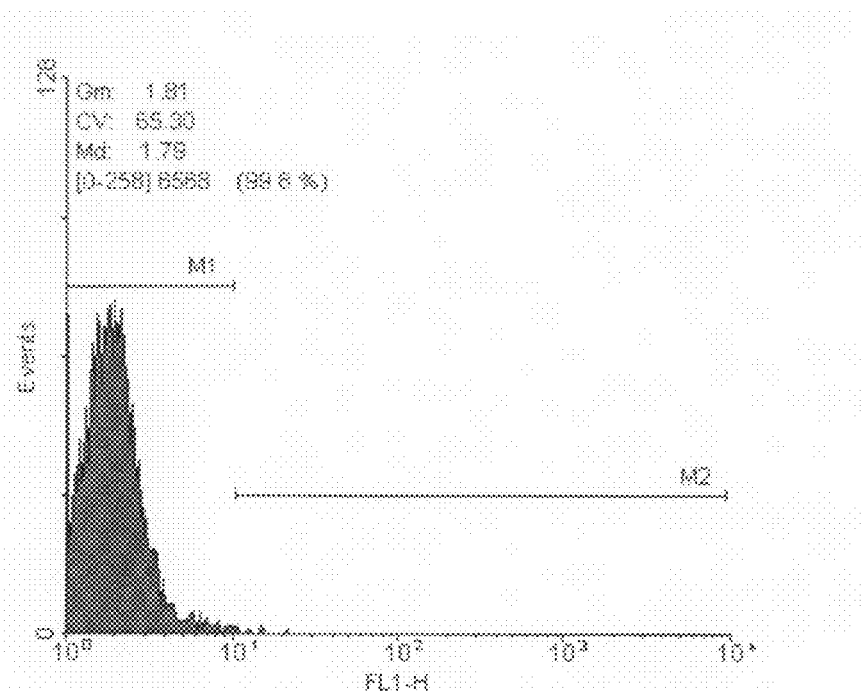
FIG. 3 shows the fluorescence of zymosan-FITC binding with HEK293 cells with (FIG. 3B) or without (FIG. 3A) transfection of Dectin-1 expression vectors. Cells were stained with FITC-zymosan.
Figure 3B:
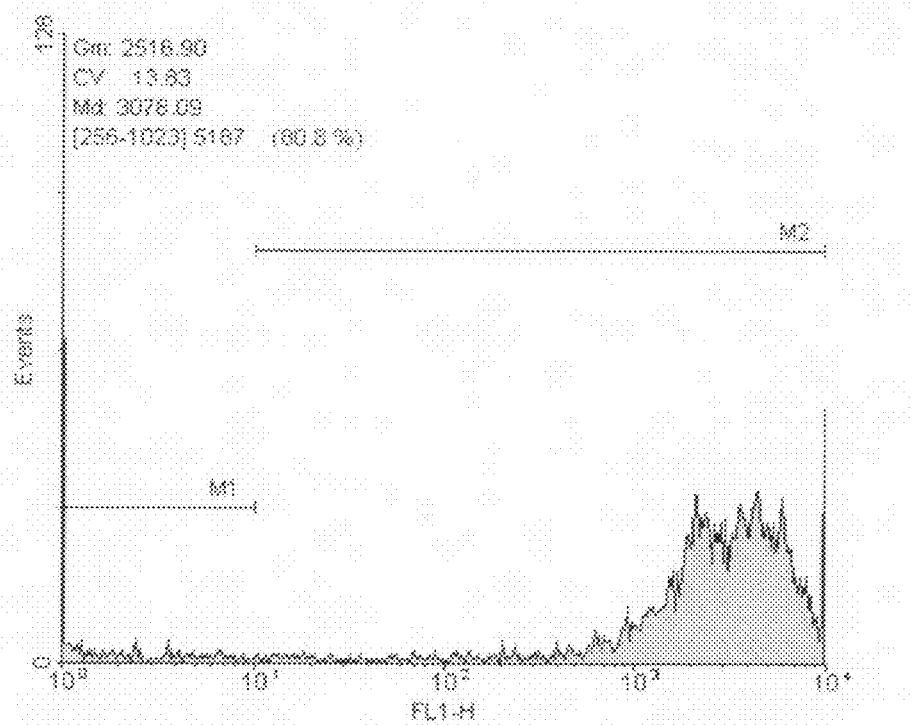
Figure 4A:
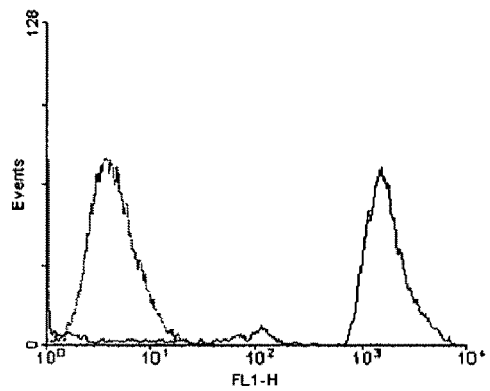
FIG. 4 shows the fluorescence of zymosan-FITC binding with hDectin-1-transduced HEK293 cells. The cells with (□) or without (□) transfection of human Dectin-1 expression vector were stained with zymosan-FITC (FIG. 4A). Certain amounts of zymosan-FITC competed with different dilutions of yeast beta-glucan of 50, 100, 300, 500, and 700 μg/mL (FIGS. 4B to 4F) to bind with hDectin-1-transduced HEK293 cells.
Figure 4B:
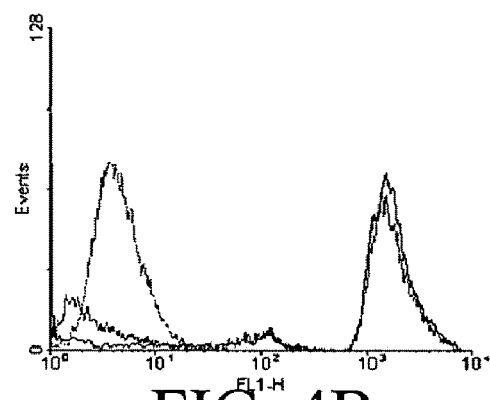
Figure 4C:
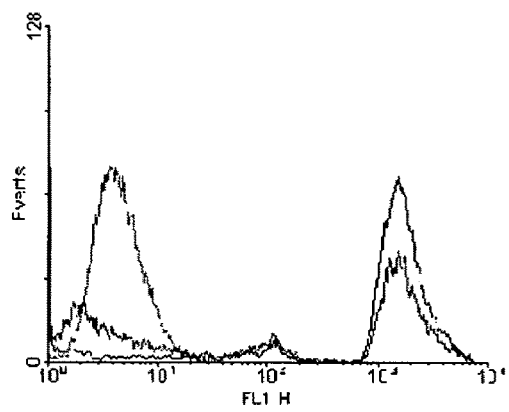
Figure 4D:
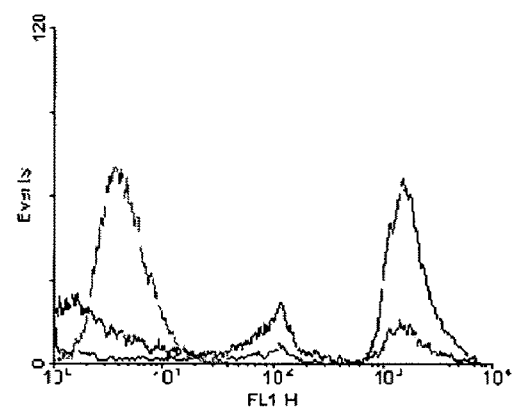
Figure 4E:
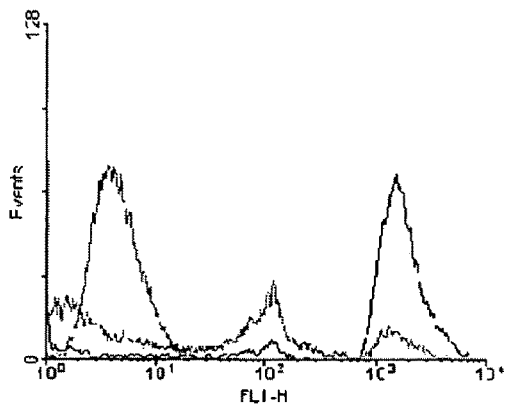
Figure 4F:
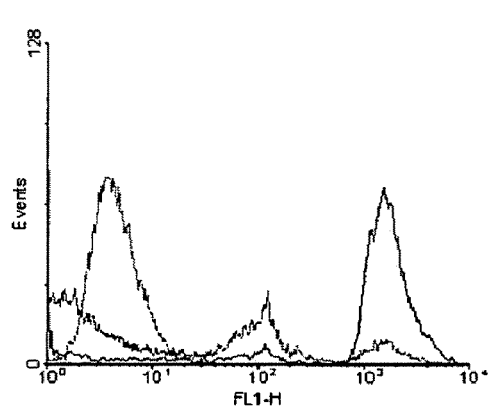

The cells were also assayed with a flow cytometry, and shown in FIG. 3. It is shown that FITC-zymosan has the ability to bind to HEK293 expressing human dectin-1 gene, while no fluorescence signal is detected in the HEK293 without human dectin-1 gene.

Standard Beta-Glucan

A commercialized particular yeast beta-glucan was taken as a standard beta-glucan. Various concentrations of 0.05 mg/ML, 0.1 mg/ML, 0.3 mg/mL, 0.5 mg/mL and 0.7 mg/mL were provided.

The test cell line was cultured at 37° C./5% $CO_2$ for two days, and then the cells were suspended. $3\times10^5$ cells/mL of the test cell line were added to the standard beta-glucan and reacted at 4° C. for 1 hour. After washing with PBS, the marker beta-glucan (10 particles/cell) was added and reacted at 4° C. for 30 minutes. The un-reacted marker beta-glucan was removed by washing with PBS and the test cell line was collected in 1 mL of PBS and analyzed with a flow cytometry. The result is shown in FIG. 4, and the fluorescence strength decreases with the increase in the standard beta-glucan.

Regression Curve

Figure 5:
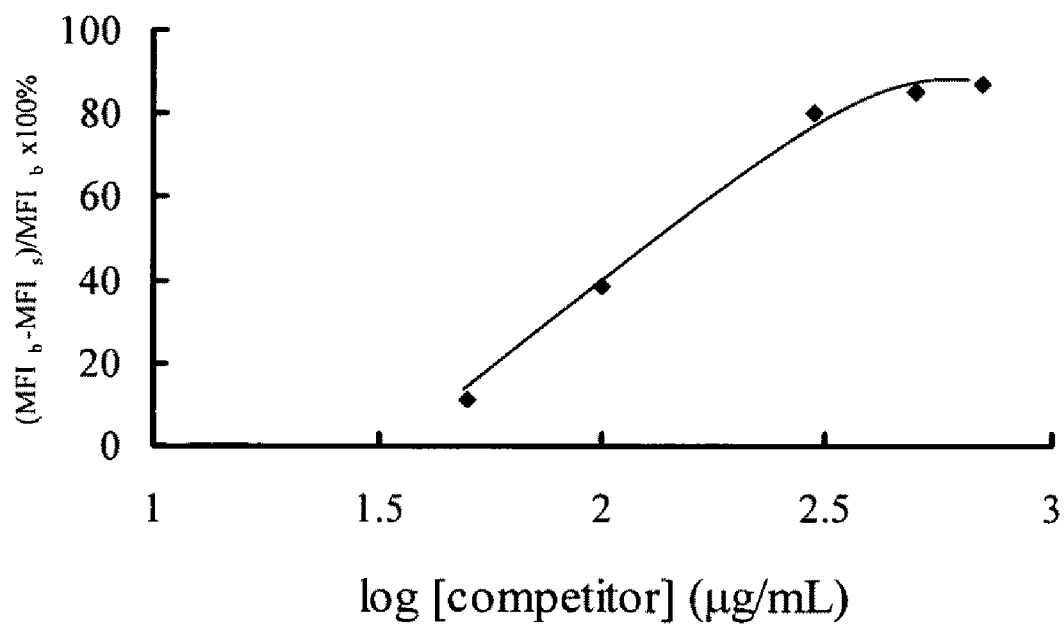
FIG. 5 shows the competitive receptor binding assay for quantification of a biologically active beta-glucan. $MFI_b$=The mean fluorescence index of blank when 0 μg/mL of yeast beta-glucan was a competitor. $MFI_s$=The mean fluorescence index of each yeast beta-glucan when 50, 100, 300, 500 and 700 μg/mL of yeast beta-glucans were competitors.

On the basis of the result obtained as mentioned above, a regression curve was obtained and shown in FIG. 5. The linear range of the concentration is from 50 to 300 μg/mL and the percentage of competitive binding with receptors in a first order reaction (linear reaction) in this competitive receptor binding assay is from 10% to 80%. When the concentration of the standard beta-glucan is less than 50 μg/mL, the competitive binding is less than 10%. When the concentration of the standard beta-glucan is between 50 to 300 μg/mL, the equation of regression curve is y=88.4x−138.8 ($y=(MFI_b-MFI_s)/MFI_b \times 100\%$; x=log [competitor] and regression coefficient is 0.9999. $MFI_b$=The mean fluorescence index of blank while the 0 μg/mL of yeast beta-glucan was a competitor. $MFI_s$=The mean fluorescence index of each yeast beta-glucan. It shows that the method according to the invention is qualified to quantify a beta-glucan having immunomodulatory activity in a human cell.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the following claims.

What is claimed is:

1. A method for detecting a beta-glucan which comprises the steps of:
   (a) providing a test mixture comprising:
   a test cell line that stably expresses human dectin-1 molecule on the cell surface and does not express other glucan receptors, wherein the test cell line is derived from a kidney and attached to the surface of a carrier,
   a sample, and
   a marker beta-glucan that specifically binds to human dectin-1 molecule, wherein
   the marker beta-glucan comprises a detectable molecule;
   (b) contacting the sample and a specific amount of the marker beta-glucan in a test mixture under conditions that allow a complex between the marker beta-glucan or beta-glucan (if any present) and dectin-1 to form;
   (c) contacting the specific amount of the marker beta-glucan with the test cell line in a reference mixture under conditions that allow a complex between the market beta-glucan and dectin-1 to form;
   (d) removing the sample and the marker beta-glucan which do not form a complex with the test cell line in the test mixture in (b) and the reference mixture in (c);
   (e) detecting the amounts of the bound marker beta-glucan in the test mixture and the reference mixture; and
   (f) comparing the amount of the marker beta-glucan in the test mixture and that in the reference mixture, wherein the sample is identified to contain the beta-glucan having immunomodulatory activity in a human cell when the amount of the bound marker beta-glucan in the test mixture is less than that in the reference mixture.

2. The method according to claim 1, wherein the test cell line is a transformed cell line transformed with human dectin-1 gene.

3. The method according to claim 1, wherein the sample is derived from food.

4. The method according to claim 1, wherein the marker beta-glucan has a beta 1,3 and a beta 1,6 linkages.

5. The method according to claim 4, wherein the marker beta-glucan is selected from the group consisting of zymosan, laminarin, glucan phosphate, pustulan, lichenan, scleroglucan and barley glucan.

6. The method according to claim 1, wherein the said detectable molecule is selected from the group consisting of a dye, an enzyme, or a reporter protein.

7. The method according to claim 1, wherein the marker comprises a molecule selected from the group consisting of fluorescein isothiocyanate, allophycocyanin, phycoerythrin, cyanine-3, cyanine-5, biotin, horseradish peroxidase, and beta-glucosidase.

8. The method according to claim 1, which is carried out with an enzyme-linked immunosorbent assay system.

9. The method according to claim 1, which is for quantifying a beta-glucan amount wherein
   step (a) further comprises providing standard mixtures comprising known amounts of a beta-glucan standard that specifically binds to human dectin-1 molecule;
   steps (b) and (c) further comprise contacting said standard mixtures and the marker beta-glucan with the test cell line in said standard mixtures under conditions that allow a complex between the market or standard beta-glucan and dectin-1 to form;
   step (d) further comprises removing the beta-glucan standard and the marker beta-glucan which do not form a complex with the test cell line in the standard mixtures;
   step (e) further comprises detecting the amount of the bound marker beta-glucan in the standard mixtures; and generating a regression curve of a quantitative indicator of the detectable marker standard versus the amount of the marker beta-glucan; and
   step (f) further comprises quantifying the amount of the beta-glucan by comparing the amount of the marker beta-glucan in the test mixture and the regression curve in step (e).

10. The method according to claim 9, wherein the standard beta-glucan has a beta 1,3 and a beta 1,6 linkages.

11. The method according to claim 10, wherein the standard beta-glucan is selected from the group consisting of zymosan, laminarin, glucan phosphate, pustulan, lichenan, scleroglucan and barley glucan.

* * * * *